United States Patent
Sumrall et al.

(10) Patent No.: US 9,504,252 B2
(45) Date of Patent: Nov. 29, 2016

(54) MICROBIOCIDES AND USES THEREOF

(71) Applicant: Buckman Laboratories International, Inc., Memphis, TN (US)

(72) Inventors: Theodore S. Sumrall, Fort Walton Beach, FL (US); Thomas E. McNeel, Memphis, TN (US)

(73) Assignee: BUCKMAN LABORATORIES INTERNATIONAL, INC., Memphis, TN (US)

( * ) Notice: Subject to any disclaimer, the term of this patent is extended or adjusted under 35 U.S.C. 154(b) by 0 days.

(21) Appl. No.: 14/813,253

(22) Filed: Jul. 30, 2015

(65) Prior Publication Data
US 2016/0029634 A1 Feb. 4, 2016

Related U.S. Application Data (60) Provisional application No. 62/032,095, filed on Aug. 1, 2014.

(51) Int. Cl.
| | | |
|---|---|---|
| *A01N 47/14* | (2006.01) | |
| *C09K 8/035* | (2006.01) | |
| *C09K 8/60* | (2006.01) | |
| *C09K 8/54* | (2006.01) | |

(52) U.S. Cl.
CPC ............... *A01N 47/14* (2013.01); *C09K 8/035* (2013.01); *C09K 8/605* (2013.01); *C09K 8/608* (2013.01); *C09K 8/54* (2013.01); *C09K 2208/32* (2013.01)

(58) Field of Classification Search
IPC .................................. A01N 47/14,41/12, 47/46
See application file for complete search history.

(56) References Cited

U.S. PATENT DOCUMENTS

| | | | | |
|---|---|---|---|---|
| 3,699,231 A | * | 10/1972 | Werlein | ................. A01N 47/14 514/492 |
| 3,856,851 A | | 12/1974 | Buckman et al. | |
| 5,075,332 A | * | 12/1991 | Haglund | ................. A01N 47/14 514/476 |
| 5,575,928 A | * | 11/1996 | Peltier, Jr. | ................. C02F 1/50 210/764 |
| 7,906,463 B2 | | 3/2011 | Starkey, II et al. | |
| 2013/0190214 A1 | | 7/2013 | Kolari et al. | |
| 2014/0088190 A1 | | 3/2014 | McNeel et al. | |

FOREIGN PATENT DOCUMENTS

| | | |
|---|---|---|
| EP | 0337624 A2 | 10/1989 |
| EP | 0 729 701 A2 | 9/1996 |
| JP | H07-145011 A | 6/1995 |
| JP | 2000-281942 A | 10/2000 |
| WO | 2012/125890 A2 | 9/2012 |

OTHER PUBLICATIONS

Written Opinion and International Search Report of PCT/US2015/042793 Dated Jul. 30, 2015.

* cited by examiner

*Primary Examiner* — Shirley V Gembeh
(74) *Attorney, Agent, or Firm* — McBee Moore Woodward Vanik IP LLC (57) ABSTRACT

The compositions and methods for control of microbial growth, for example, in oil and gas field fluids. The present invention also relates to microbicides, and more particularly, to the use of biocides in gas and oil field fluids.

27 Claims, 4 Drawing Sheets

MICROBIOCIDES AND USES THEREOF

CROSS REFERENCE TO RELATED APPLICATIONS

The present application claims priority to Provisional U.S. Patent Application 62/032,095 filed Aug. 1, 2014. The provisional application is incorporated by reference in its entirety.

BACKGROUND

Field of the Invention

The present invention relates to compositions and methods for control of microbial growth, for example, in oilfield compositions. The present invention also relates to microbicides, and more particularly, to the use of biocides in gas and oil field well fluids, for example, fluids used in drilling operations, stimulation operations, and/or post stimulation activities such as produced and flowback waters.

Description of Related Art

The production of oil from oilfields involves several phases. Most of these phases can be affected with unwanted microbial activity. Also, in other industries, there can be problems of microbial contamination. There is an ongoing need for improved methods and compositions for controlling these undesired microorganisms.

After a well is drilled into a subterranean geological formation that contains oil, natural gas, and water, every effort is made to maximize the production of the oil and/or gas. To increase the permeability and flow of the oil and/or gas to the surface, the drilled wells are often subjected to well stimulation.

Well stimulation generally refers to several post drilling processes used to clean the well bore, enlarge channels, and increase pore space in the interval to be injected thus making it possible for fluids to move more readily into the formation.

A typical well treatment process generally includes pumping specially engineered fluids at high pressure and rate into the subterranean geological formation. The high-pressure fluid (usually water with some specialty friction reducing fluid additives to reduce pumping pressure and maximize rock fracturing) exceeds the rock strength and opens a fracture in the formation, which can extend out into the geological formation for as much as several hundred feet. Certain commonly used fracturing treatments generally comprise a carrier fluid (usually water or brine) and a polymer, which is also commonly referred to as a friction reducer. Many well stimulation fluids will further comprise a proppant. Other compositions used as fracturing fluids include water with additives, viscoelastic surfactant gels, gelled oils, crosslinkers, oxygen scavengers, and the like.

The well treatment fluid can be prepared by blending the polymer with an aqueous solution (sometimes an oil-based or a multi-phase fluid is desirable); often, the polymer is a solvatable polysaccharide. The purpose of the polymer is generally to decrease the turbulent frictional forces of the fracturing fluid that aids in the creation of a fracture; and to sufficiently thicken the aqueous solution so that solid particles of proppant can be suspended in the solution for delivery into the fracture.

The polymers used in well fluids are subjected to an environment conducive to bacterial growth and oxidative degradation. The growth of the bacteria on polymers used in such fluids can materially alter the physical characteristics of the fluids. For example, bacterial action can degrade the polymer, leading to loss of viscosity and subsequent ineffectiveness of the fluids and, more importantly, lead to the plugging of the fracture (due to biofilms growth) and subsequent reduction in recovery of the desired hydrocarbons. Fluids that are especially susceptible to bacterial degradation include those that contain polysaccharide and/or synthetic polymers such as polyacrylamides, polyglycosans, carboxyalkyl ethers, and the like. In addition to bacterial degradation, these polymers are susceptible to oxidative degradation in the presence of free oxygen. The degradation can be directly caused by free oxygen or mediated by aerobic microorganisms. Thus, for example, polyacrylamides are known to degrade to smaller molecular fragments in the presence of free oxygen. Because of this, microbicides and oxygen scavengers are frequently added to the well treatment fluid to control bacterial growth and oxygen degradation, respectively. Desirably, the microbicide is selected to have minimal or no interaction with any of the components in the well stimulation fluid.

For example, the microbicide should not affect fluid viscosity to any significant extent and should not affect the performance of oxygen scavengers, often derived from bisulfite salts, contained within the fluid. However, a reduced viscosity can be overcome by additional polymer and/or crosslinkinker addition. This situation is more desirable than an increased viscosity.

Other desirable properties for the microbicide are (a) cost effectiveness, e.g., cost per liter, cost per square meter treated, and cost per year; (b) safety, e.g., personnel risk assessment (for instance, toxic gases or physical contact), neutralization requirements, registration, discharge to environment, and persistence; (c) compatibility with system fluids, e.g., solubility, partition coefficient, pH, presence of hydrogen sulfide, temperature, hardness, presence of metal ions or sulfates, level of total dissolved solids; (d) compatibility with other treatment chemicals, e.g., corrosion inhibitors, scale inhibitors, demulsifiers, water clarifiers, well stimulation chemicals, and polymers; and (e) handling, e.g., corrosiveness to metals and elastomers, freeze point, thermal stability, and separation of components.

Current well stimulation fluids often employ either glutaraldehyde, or tetra-kis-hydroxymethyly-phosphonium sulfate (THPS), or 2,2-dibromo-3-nitrilopropionamide (DB-NPA), or other fast acting biocides to control bacterial contamination.

A common industry practice is to control microbial growth by adding an effective amount of a quick kill biocides followed by controlled sequential addition of another relatively slower acting biocide. Illustrative of quick-kill biocides include alkanedials for example lower alkanedials such as $C_1$-$C_8$ alkane dials such as propanedial, butanedial, pentanedial, hexanedial, and the like. Preferred is DBNPA and pentanedial (glutaraldehyde).

It is also well known within the industry to use a quick kill biocide (such as glutaraldehyde), followed within minutes, hours, or days, by a relatively slower acting biocide to reduce or inhibit microbial activity. For instance, EP0337624B 1 teaches a method of controlling oilfield biofouling, comprising adding an effective amount of quick kill biocide selected from one or more alkanedials, for example $C_3$-$C_7$ alkanedials, and then adding, by controlled sequential addition, an effective amount of isothiazolone, which functions as a slower acting biocide.

Glutaraldehyde (pentanedial) can be problematic to use because it is hazardous to handle and has environmental concerns. Moreover, it has been reported in the literature that glutaraldehyde can deleteriously affect the fluid viscosity of the well treatment fluid at elevated temperatures; temperatures that are commonly observed during use of the well treatment fluid. This can be problematic in fracturing applications since the higher maintained fluid viscosity down hole could hinder flow back. In addition, glutaraldehyde has been shown to negatively impact the behavior of the oxygen scavenger.

With regard to THPS, although it has been shown to perform better than glutaraldehyde with respect to interaction with the oxygen scavengers, THPS has been found to interact with the polymer and limit viscosity development when added pre-inversion and post-inversion. That is, THPS has been observed to interact with the polymer during shear and significantly reduce fluid viscosity.

Thus, there remains a need for a more versatile microbiocide for use, for example, in oil and gas wells, that can effectively control bacterial contamination and have minimal interaction with the polymer and/or oxygen scavenger. The present invention addresses these and other needs.

SUMMARY OF THE INVENTION

In accordance with the present invention there has been provided a composition comprising (a) an effective microbial inhibiting amount of a microbicide selected from the group consisting of (i) monomethyldithiocarbamate (MMDTC), (ii) dimethyldithiocarbamate (DMDTC), (iii) salts of MMDTC or DMDTC, and (iv) mixtures and combinations thereof, and (b) optionally a polymer.

In accordance with the present invention, there has also been provided a method for inhibiting bacterial contamination, for example, in an oil or gas well fluid composition for injection into a well, such as a production well, comprising adding (a) an effective bacterial inhibiting amount of a microbicide selected from the group consisting of (i) monomethyldithiocarbamate (MMDTC), (ii) dimethyldithiocarbamate (DMDTC), (iii) salts of MMDTC or DMDTC, and (iv) mixtures and combinations thereof, and (b) optionally a polymer selected, for example, from the group consisting of galactomannan polymers, derivatized galactomannan polymers, starch, xanthan gums, hydroxycelluloses, hydroxyalkyl celluloses, polyglycosans, carboxyalkyl ethers, polyvinyl alcohol polymers, copolymers of vinyl alcohol and vinyl acetate, and polymers that are a product of a polymerization reaction comprising one or more monomers selected from the group consisting of vinyl pyrrolidone, 2-acrylamido-2-methylpropanesulfonic acid, acrylic acid, methacrylic acid, styrene sulfonic acid, acrylamide, and other monomers used for oil well treatment polymers.

Further objects, features, and advantages of the invention will become apparent from the detailed description that follows.

DETAILED DESCRIPTION OF THE DRAWINGS

The present invention may be more fully understood with reference to the accompany figures. The figures are intended to illustrate exemplary features of the invention without limiting its scope.

DETAILED DESCRIPTION

The present invention relates to compositions including one or more microbicides selected from MMDTC and DMDTC and salts thereof. The salts can include any water-soluble salt of monomethyldithiocarbamate (MMDTC) ion and/or dimethyldithiocarbamate (DMDTC) ion, including but not limited to any alkali metal or alkaline earth metal salts, such as lithium, sodium, potassium, magnesium, and calcium. Salts of sodium, potassium, and/or calcium are preferred. The salts can also be any quaternary ammonium salt thereof. The biocides of the invention can be used in any environment where it is desired to control bacteria. For example, in fluids, such as, well stimulation fluids, used in oil and gas wells. The microbicide of the invention is used in an in an amount effective to inhibit or control bacterial growth. The biocides of the invention can be the sole biocide or biocides in the composition or used in combination with other biocides.

MMDTC or its salts can be used alone or in combination with DMDTC. DMDTC or its salts can be used alone or in combination with MMDTC. Mixtures of different salts can be used. Any combination of MMDTC and DMDTC, including salts of either can be used. MMDTC can be combined with DMDTC. Relative to many microbicides currently used in well stimulation fluids, MMDTC, DMDTC, as well as MMDTC+DMDTC appear to be much more versatile and provide a reduced interference with friction reducers in the well fluid, a reduced interference with oxygen scavengers, such as sulfite-based oxygen scavengers, and has minimal interaction with friction reducers at elevated temperatures relative to conventional microbicides such as glutaraldehyde. MMDTC and/or DMDTC can be added to the fluid in any desired format, for example, as an emulsified fluid.

Any desired combinations of MMDTC and DMDTC can be used. For example, they can be used alone, or as their water-soluble salts, or combined in any desired proportions. For example, the biocide can comprise a weight ratio of sodium or potassium monomethyldithiocarbamate (MMDTC) to sodium or potassium dimethyldithiocarbamate (DMDTC) of from 10:90 to 100:0, or from 10:90 to 95:5, or from 80:20 to 20:80 or from 70:30 to 30:70. Ratios of (MMDTC) to (DMDTC) 50:50 to 95:5; or 60:40 to 90:10 or 65:35 to 80:20 or 75:25 to 95:5 or 60:40 to 80:20 can also be used. The biocide or combinations of biocides can be present in amounts such that there is a synergistic effect on the inhibition of bacterial growth The biocides can be included in fluid compositions and used to inhibit bacterial growth in well drilling, stimulation, production, and/or post-production, and/or any other fluids associated with the industrial process where it is desired to control or inhibit bacterial growth. The biocides of the invention can be used, for example, in those composition described above in the Background Section of this application. In one embodiment, the fluid comprises water; and a polymer. The polymer can be any polymer used in well fluids. Examples of polymers include galactomannan polymers, derivatized galactomannan polymers, starch, xanthan gums, hydroxycelluloses, hydroxyalkyl celluloses, polyvinyl alcohol polymers, copolymers of vinyl alcohol and vinyl acetate, and polymers that are a product of a polymerization reaction comprising one or more monomers selected from the group consisting of vinyl pyrrolidone, 2-acrylamido-2- methylpropanesulfonic acid, acrylic acid, methacrylic acid, styrene sulfonic acid, acrylamide and other monomers currently used for oil well treatment polymers.

It has also been found that in a method for inhibiting bacterial contamination in a well fluid comprising adding an effective bacterial inhibiting amount of a microbicide of MMDTC or salt thereof, to the well stimulation fluid with the option of combining DMDTC or salt thereof, there has been shown to be a synergistic effect on MMDTC.

The well fluid preferably comprises at least one polymer. Preferred classes of polymers include polysaccharides or synthesized polymers. Suitable polymers include, those mentioned above, as well as, but not limited to, galactomannan polymers and derivatized galactomannan polymers; starch; xanthan gums; hydroxycelluloses; hydroxyalkyl celluloses; polyvinyl alcohol polymers (such as homopolymers of vinyl alcohol and copolymers of vinyl alcohol and vinyl acetate); and polymers (such as homopolymers, copolymers, and terpolymers) that are the product of a polymerization reaction comprising one or more monomers selected from the group consisting of vinyl pyrrolidone, 2-acrylamido-2-methylpropanesulfonic acid, acrylic acid and acrylamide, methacrylic acid, styrene sulfonic acid, acrylamide and other monomers currently used for oil well treatment polymers, among others. Certain polyvinyl alcohol polymers can be prepared by hydrolyzing vinyl acetate polymers. Preferably the polymer is water-soluble. Specific examples of polymers that can be used include, but are not intended to be limited to hydrolyzed polyacrylamide, guar gum, hydroxypropyl guar gum, carboxymethyl guar gum, carboxymethylhydroxypropyl guar gum, hydroxyethyl cellulose, carboxymethylhydroxyethyl cellulose, hydroxypropyl cellulose, copolymers of acrylic acid and acrylamide, xanthan, starches, and mixtures thereof, among others.

The amount of MMDTC and/or DMDTC and/or their salts in the well fluid will vary, generally depending on the polymer employed, the conditions of the water and the extent of prior bacterial growth, the time period of bacterial growth, general environment where the microbicide will be used, and the like. Thus, it is generally not possible to delineate a minimal amount, however, one skilled in the art will be able to determine the minimal amount without undue experimentation. There is no maximum, amount, although large excess may not be desirable for economic and/or environmental reasons.

The MMDTC, DMDTC, and/or MMDTC+DMDTC can be used in any form. For example, added directly as an emulsification, solid, or solution to the fluid used to make the well stimulation fluid, added to a concentrated polymer solution, and/or may be made on a slug dose basis. The present disclosure is not intended to be limited to a particular method for making the well stimulation fluid.

Examples of bacteria and/or archaea to which the claimed compositions are effective include those commonly found in oil and gas field fluids and waters include, but are not limited to, aerobic and non-aerobic bacteria/archaea, sulfate reducing bacteria/archaea, acid producing bacteria/archaea, general heterotrophic bacteria/archaea, and the like. Specific examples include, but are not limited to, *pseudomonad* species, *bacillus* species, *enterobacter* species, *serratia* species, *clostridia* species, and the like. It should be noted that it is expected that the use of MMDTC, DMDTC, and/or or MMDTC+DMDTC in the well fluid will be effective to inhibit algae and fungi formation at the same biocidal concentrations for bacterial effectiveness.

Well drilling, production, stimulation, completion and/or treatment fluid and other compositions of the invention compositions of the present invention can further include one or more additives. Additives are generally included to enhance the stability of the fluid composition itself to prevent breakdown caused by exposure to oxygen, temperature change, trace metals, constituents of water added to the fluid composition, and to prevent non-optimal crosslinking reaction kinetics. The choice of components used in fluid compositions is dictated to a large extent by the properties of the hydrocarbon-bearing formation on which they are to be used. Such additives can include water, oils, salts (including organic salts), crosslinkers, polymers, other microbicides, corrosion inhibitors and dissolvers, pH modifiers (e.g., acids and bases), breakers, metal chelators, metal complexors, antioxidants, wetting agents, surfactants, polymer stabilizers, clay stabilizers, scale inhibitors and dissolvers, wax inhibitors and dissolvers, asphaltene precipitation inhibitors, water flow inhibitors, oxygen scavengers, fluid loss additives, chemical grouts, diverters, sand consolidation chemicals, proppants, permeability modifiers, viscoelastic fluids, gases (e.g., nitrogen and carbon dioxide), and foaming agents. Also, the composition of the invention can be free of one or more of these typical additives, for example, free of bases, such as hydroxides. The biocides of the invention can be isolated from other chemicals and present by themselves, or include other additives such as mentioned above. The biocides of the present invention can include, for example, glutaraldehyde or tetra-kis-hydroxymethyly-phosphonium sulfate (THPS) or 2,2-dibromo-3-nitrilopropionamide (DBNPA) or other fast acting biocides.

The biocides of the present invention can be used in combination, including sequentially or together, with other biocides. For example, an effective amount of a quick kill biocides can be used followed by controlled sequential addition of another relatively slower acting biocide MMDTC and/or MMDTC and/or salts thereof according to the invention. Illustrative of quick-kill biocides include alkanedials for example, lower alkanedials such as $C_1$-$C_8$ alkane dials such as propanedial, butanedial, pentanedial, hexanedial, and the like. Preferred fast-acting biocides include DBNPA and pentanedial (glutaraldehyde). The quick kill biocide, can be followed within minutes, hours, or days, by a relatively slower acting biocide according to the invention, to reduce or inhibit microbial activity. In addition to this sequential method, the biocides of the invention can also be admixed and used together with other biocides, such as with any biocide that has been used in the oil and gas field.

While this disclosure focuses on the oil and gas industry, the biocides of the invention can be used in any environment or industry, where it is desired to control, inhibit, and/or kill bacteria and/or archaea. The biocides can be introduced at any time or any location in the process to effectively control bacteria and/or archaea. For example, for well stimulation, the fluid containing the biocide of the invention, can be injected directly into the well bore to react with and/or dissolve substances affecting permeability; injected into the wellbore and into the formation to react with and/or dissolve small portions of the formation to create alternative flowpaths; and/or injected into the well bore and into the formation at pressures effective to fracture the formation.

In some embodiments, the well fluid has a viscosity substantially the same as a control well stimulation fluid without the microbicide. For example, the fluid preferably has a viscosity plus or minus 10%, or within 5%, or within 2% of the viscosity of the fluid without the biocide.

The fluid composition of the invention can be injected into an injection zone, wherein the injection zone includes a)

a geologically produced material that contains one or more solid, liquid, or gaseous hydrocarbons; b) a hydrocarbon deposit; c) a petroleum deposit; d) a hydrocarbon or petroleum product formation; e) a hydrocarbon, or petroleum containing product; f) a hydrocarbon, or petroleum extraction site including drilling, hydraulic fracturing, production, stimulation, and/or disposal sites; g) hydrocarbon or petroleum transportation facility or storage equipment including pipeline, mobile tanker loading facilities, storage tanks and/or h) a refining facility, products, processes, equipment, or combinations thereof and waters and fluids associated with: drilling; stimulation; production; hydraulic fracturing; and/or disposal.

The injection zone can include (i) makeup waters or fluids (ii) recycled waters or fluids (iii) flowback waters or fluids, (iv) injection waters or fluids, (v) produced waters or fluids or (vi) other waters or fluids found or employed in oil field: drilling; stimulation; hydraulic fracturing; production and/or disposal operations, in an amount sufficient to reduce, inactivate, destroy, or eliminate microbes of interest.

In addition to in oil and gas field application, the composition can be used in an environment and industry or system where it is desired to control bacteria.

The present invention is illustrated by the following non-limiting examples.

Example 1

In this example, the post inversion viscosity of a polymeric fluid having a biocide at different concentrations was analyzed relative to a control that did not include a biocide. The biocides analyzed included glutaraldehyde (GA), sodium-N-methyldithiocarbamate (SNMDTC), potassium-dimethyldithiocarbamate (PDMDTC) and a combination of SNMDC and PDMDTC at a ratio of 80:20. A 0.1% active aqueous stock solution of polyacrylamide (PAM) (with a molecular weight of approximately 15M Daltons) was made and allowed to age for about 30 minutes. For each of the samples tested, 200 milliliters of the stock solution was taken to which the biocide was added at various concentrations and subjected to rapid shearing via a blender at the lowest setting for five seconds and then the mixture viscosity measured by a Brookfield viscometer. The samples were considered equilibrated at the ten second mark (as only minimal changes occurred after 10 seconds of rotation of the viscometer spindle) and the value was recorded. The biocide was added at concentrations of 250, 500, 750 and 1,000 parts per million (ppm) and subjected to high shear in a blender (at the lowest setting) for five seconds after which time the viscosity was recorded.

Figure 1:
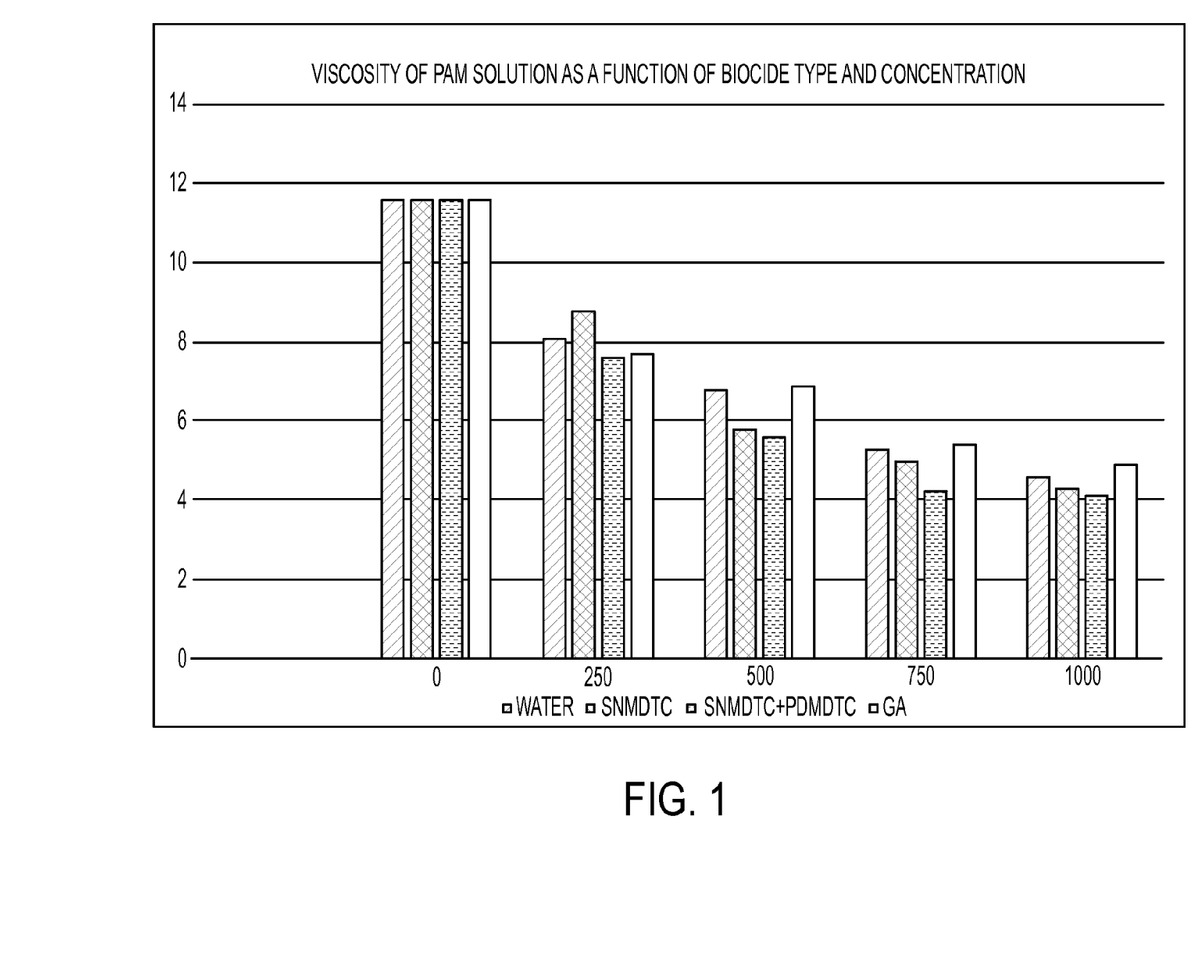
FIG. 1 is bar graph illustrating the viscosity of solutions as a function of biocide type and concentration.

The test results are graphically illustrated in FIG. 1. As shown, polymer viscosity is observed as a function of biocide concentration. At lower concentrations (ex. 250 ppm) the viscosities of GA and the combination of SNMDTC and PDMDTC were slightly lower than the control with only additional sterile water added. The viscosity of the SNMDTC was slightly higher. However, at higher concentrations the viscosities of the SNMDTC and the combination of SNMDTC and PDMDTC were slightly lower than the control and the sample containing GA. This finding is significant because the active ingredient in GA (glutaraldehyde) is a biocide commonly utilized in the oil and gas industry because of its lack of negative impact on polymers such as polyacrylamide (PAM). It was found that the SNMDTC as well as the combination of SNMDTC and PDMDTC have viscosities which are approximately 2.75% lower than with GA. It was observed that the combination of SNMDTC and PDMDTC had the lowest viscosity of all the biocides tested.

The reduced viscosity is not to be considered a problem as additional cross linking agent and/or polymer may be added to compensate for this reduction if needed. What is important is that the viscosity did not increase which could (in hydraulic fracturing applications) be problematic since the higher maintained viscosity down hole could potentially hinder flow back.

Example 2

In this example, the effect of heat on the biocide/polymer fluids and control of Example 1 was analyzed. The biocides tested included: Glutaraldehyde (GA); sodium-N-methyldithiocarbamate (SNMDTC); potassium-dimethyldithiocarbamate (PDMDTC); a blend of SNMDTC and PDMDTC and a control. Some biocides can have an adverse effect on polymers causing them to be more viscous than desired which in fracturing applications is undesirable since the higher maintained viscosity down hole could potentially hinder flow back. For each of the samples that were tested, 1,000 ppm of the biocide was added to 200 grams of the polyacrylamide stock solution of Example 1. The samples were blended for 5 seconds (at a low setting but a high shear) and the viscosity measured. The samples were then placed into an oven at 140° F. for 24 hours, and were allowed to cool to room temperature (77° F.).

Figure 2:
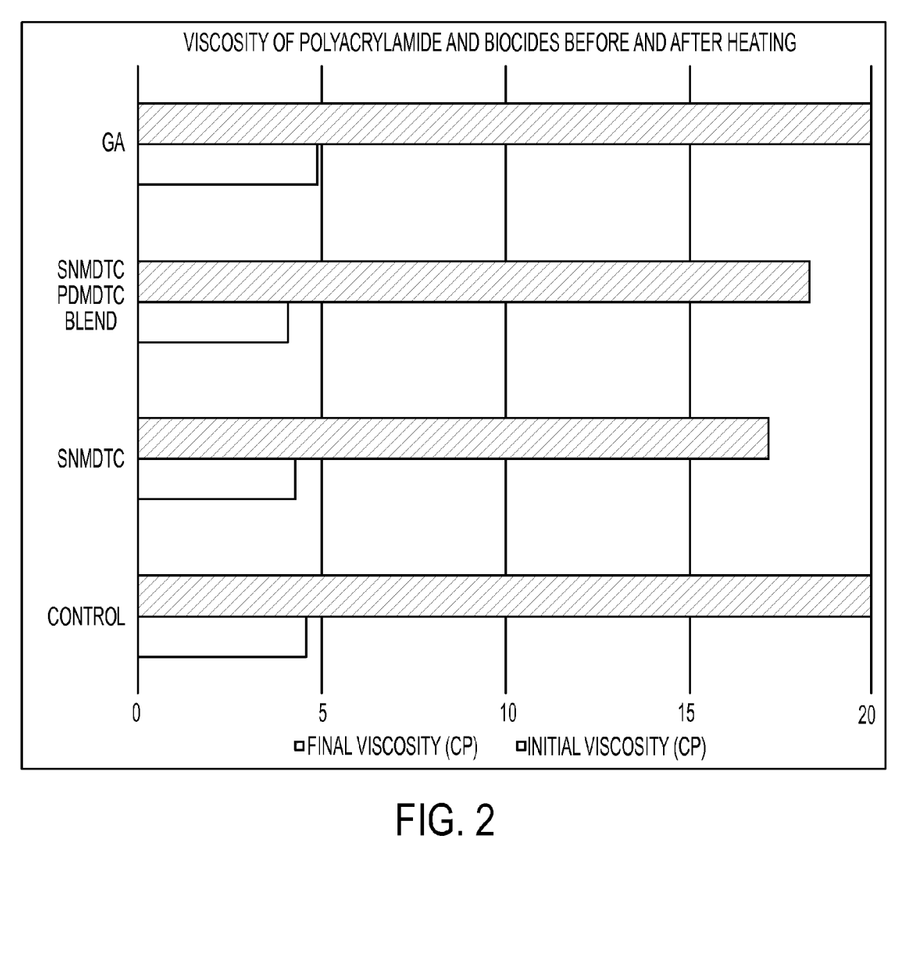
FIG. 2 is a bar graph illustrating the viscosity of polyacrylamide and biocide blends before and after heating.

Once the samples were at room temperature, deionized water was added to return the volume back to the original volume (due to water evaporation while in the oven) and the samples were blended for 5 seconds (at a low setting but a high shear) and the viscosity was measured. The results are shown in FIG. 2.

From the results, it is observed that polymer viscosity increased with heat over time for all samples. However, the viscosities of each sample also varied as a function of biocide type added. For each test, the initial viscosity measurement shows only the effect of the biocide on the polymer viscosity relative to a sample without biocide (identified as the "Control") while the second reading took into account the effect of the biocide and heat on viscosity.

It was observed that the SNMDTC and the PDMDTC combination actually resulted in a small reduction in viscosity compared to the control both initially as well as after heating which was anticipated given the results seen in the previous viscosity testing. This reduction is not considered to be a problem as additional cross linking agent and/or additional polymer may be added to compensate for this reduction if needed. What is important is that the viscosity did not increase which could (in hydraulic fracturing applications) be problematic since the higher maintained viscosity down hole could potentially hinder flow back.

After 24 hours at 140° F., however, the viscosities of the control (Blank) SNMDTC and the SNMDTC/PDMDTC combination showed that the relative viscosity differences were approximately the same, with the straight SNMDTC having the lowest viscosity. The viscosity of the control (Blank) and the GA were approximately the same after thermal exposure.

The published literature suggests that a crosslinking may be occurring between GA and acrylamide thus accounting for its ability to maintain a higher viscosity. Again, however, a decreased viscosity (within the bounds shown herein) is better than a higher viscosity of the same magnitude.

Example 3

In this example, the effects of four different biocides: 1) sodium-N-methyldithiocarbamate (SNMDTC) by itself and 2-3) in combination with two ratios of potassium-dimethyldithiocarbamate (PDMDTC), and 4) a 25% solution of Glutaraldehyde (GA) on an oxygen scavenger was examined. To a beaker containing 500 milliliters of Butterfield Buffer solution, a 200 ppm dose of sodium sulfite ($Na_2SO_3$) as oxygen scavenger was added and the pH and oxygen reduction potential (ORP) were recorded.

Figure 3:
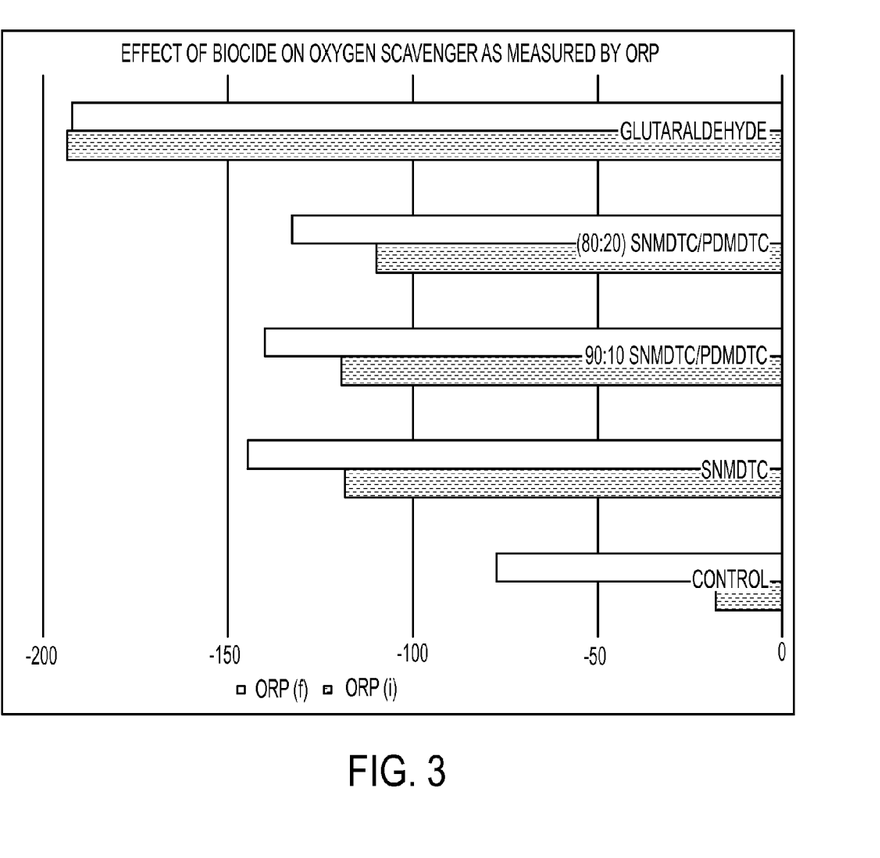
FIG. 3 is a bar graph illustrating the effect of biocide on oxygen scavenger.

Finally, the particular biocides tested was added at a concentration of 500 ppm. The ORP was recorded initially and after a period of 10 minutes. The results are shown in FIG. 3.

From these results, it can be noted that there is a significant difference in ORP response upon addition of each respective biocide. ORP is an indication of a solution's ability to oxidize or reduce another solution/species. Theoretically, the lower the ORP, the higher the ratio of reduced species to oxidized species. All of the biocides tested had an improved effect upon ORP, however, the GA showed the most improved ORP. The SNMDTC as well as the SNMDTC/PDMDTC combinations showed more than acceptable ORP properties (approximately 2× lower than the control after 10 minutes).

Example 4

In this example, biocidal effectiveness to acid producing and sulfate reducing bacteria was examined for sodium-N-methyldithiocarbamate (SNMDTC) and mixtures of SNMDTC plus potassium-dimethyldithiocarbamate (PDMDTC) at ratios of 90:10 and 80:20 respectively and at concentrations of 1000 ppm and 10,000 ppm (as product).

A one gallon sample of cone water from a contaminated drilling fluid (run through a hydrocyclone) in the DJ (Denver-Julesburg Basin) formation was employed for these studies. The cone water pH was measured at 6.4 and the redox potential was at 34.6. The sample included anaerobic sulfate reducing, aerobic and anaerobic acid producing bacteria and general heterotrophic bacteria. Both organism types were present in this sample with the $SRB+H_2S$ at levels in excess of $10^{12}$ bacteria per milliliter in the original sample.

In order to ensure that the active range was captured, the contaminated water was diluted with Butterfield phosphate buffer solution to a concentration of 0.1% of its original concentration. Serial dilutions were made using 1 cc sterile syringes to inoculate 9.0 mL anaerobic American Petroleum Institute (API) broth with an iron nail designed for sulfate reducing bacteria (SRB). In addition, Acid Producing Bacteria (APB) and General Heterotrophic Bacteria (GHB) were tested using serial dilutions in 9 mL phenol red (PR) broth. The media salinity was matched to the substrate salinity of ≈0.5% that was measured by percent Total Dissolved Solids (TDS). Additionally, an untreated control was included. In all cases the concentration was determined on a weight/weight basis of parts per million (milligrams per kilogram). Each aliquot was continuously mixed (in a thermally controlled incubator) well after the addition of the biocide and maintained at 30° C. for the duration of study.

Untreated and treated aliquots were inspected after seven days checking to see if the bottles the API bottles turned black (indicating positive SRB growth) and to see if the PRD bottles turned yellow (indicating the presence of APB) and/or turbidity (indicating the presence of GHB). A color change at the highest dilution indicated the log quantity of organisms present.

The results are shown in Table-1, wherein the counts are expressed in log values as indicated. At a level of 1,000 ppm of SNMDTC, there did not appear to be any noticeable decrease in either SRB or APB/GHB concentrations. However, at a concentration of 10,000 ppm SNMDTC the bacterial concentration of SRB decreased two log values over a period of eight days and the APB concentration decreased by one log value. However, a synergistic effect between the N-methyldithiocarbamate (SNMDTC) and the potassium-dimethyldithiocarbamate (SNMDTC) was observed. At 1,000 ppm of a 90:10 ratio of SNMDTC:PDMDTC decreased the SRB concentration by one log greater than SNMDTC alone and at a ratio of 80:20 SNMDTC:SNMDTC the SRB concentration decreased by three logs greater than SNMDTC alone.

Additionally, at 1,000 ppm biocide, SNMDTC alone did not have any noticeable effect on APB or GHB, however, a two log decrease was observed for the APB/GHB at a 90:10 ratio of SNMDTC:PDMDTC.

At 10,000 ppm of biocide any noticeable synergistic effects were overcome by the concentration of the biocides and were all below a bacterial concentration of 10 microbes per milliliter.

TABLE 1

KILL STUDY RESULTS

| Test Series | ppm Total Biocide | % SNMDTC | % PDMDTC | API SERIES | PRD SERIES |
|---|---|---|---|---|---|
| E0 | 0 | 0 | 0 | >$10^4$ | ≥$10^3$ |
| E1 | 1,000 | 100 | 0 | >$10^4$ | ≥$10^3$ |
| E3 | 10,000 | 100 | 0 | >$10^2$ | >$10^2$ |
| E4 | 1,000 | 90 | 10 | >$10^3$ | >$10^1$ |
| E5 | 10,000 | 90 | 10 | ≤$10^1$ | <$10^1$ |
| E6 | 1,000 | 80 | 20 | >$10^1$ | ≤$10^2$ |
| E7 | 10,000 | 80 | 20 | ≤$10^1$ | <$10^1$ |

Notes: Testing included both APB and GHB organisms.

Example 5

The purpose of this example was to perform compatibility testing with friction reducer and various biocides including those of the invention. The friction reducer identified as "FR-516" was evaluated on a flowloop testing apparatus at a loading of 0.5 gpt in the presence of up to 1000 ppm of biocides identified as: BSN-85 (PDMDTC), BSN-1020A (SNMDTC manufactured from carbon disulfide), BSN-1020B (SNMDTC Hi pH), BSN-1058 (SNMDTC manufactured from carbon disulfide through the intermediate step of 3,5-Dimethyltetrahydro-1,3,5,2H-thiadiazine-2-thione), dilute NaOH (pH=12) and tap water. The test samples were added to the friction loop in three separate additions to total 1000 ppm to determine if there is any detrimental effect on the friction reducer at a specific dosage level. The flowloop analysis was conducted at 24 gallons per minute through ½" diameter tubing at a Reynolds number ranging between 180,000 and 190,000. The test was conducted in tap water.

Based on the flowloop results it was concluded that the above biocides and samples are compatible with the anionic friction reducer FR-516. FR-516 is a fresh water to moderate brine FR that does not contain amps monomer. The products BSN-1020B and BSN-1058 showed the highest degree of compatibility with a total loss in friction reduction over 13 minutes of 28.2% and 28.6% respectively while the untreated control showed a total loss in reduction of 28.4%.

In this project the flowloop was operated at a flowrate of 24 gpm for a Reynolds number between 180,000 and 190,000. A baseline profile was established with 0.5 gpt FR-516 without biocide. In the method the flowloop is operated at 24 gpm for 1 minute prior to addition of the FR-516 to establish a baseline pressure. At 1 minute 0.5 gpt of FR-516 is added and the test is ran an additional twelve minutes. In the tests that included biocide 100 ppm of biocide was added to the baseline and allowed to pump for 1 minute. FR-516 was introduced at 1 minute. At 3 minutes and additional 400 ppm of biocide was added and at 5 minutes an additional 500 ppm of biocide was added for a total of 1000 ppm biocide. The test was ran for a total of 13 minutes. The test was ran through ½" OD tubing.

There is essentially no difference in the BSN-1020B and BSN-1058 treated samples vs. the control sample. The BSN-85 showed the highest degree of incompatibility with a total loss in reduction of 30.2%, and the BSN-1020A had a total loss in reduction of 29.5% over the 13 minute test period. The BSN-85 also demonstrated the highest loss in max reduction with a 1% loss in maximum reduction achieved vs. the untreated control. Overall the losses are not considered to be significant to a pumping operation based on the test results especially when compared to untreated control FR-516 is a robust fresh water to moderate brine anionic friction reducer capable of functioning in up to 40,000 mg/L TDS brine, depending on the presence and concentration of divalent cations in solution. In Broussard tap water at a loading of 0.5 gpt, without biocide, FR-516 achieved a maximum reduction of 57.0%. In the presence of 100 ppm of biocide in the baseline of the flowloop test the maximum reductions achieved were all 56% or greater, and none of the biocides appeared to delay the inversion of the friction reducer. The greatest loss in maximum reduction was in the presence of BSN-85, and the maximum loss in reduction over 13 minutes was also in the presence of BSN-85. The total loss was 30.2% from overall maximum reduction achieved. The loss is only in excess of the control by 1.8% and may be within experimental error of the test, and the overall high loss in reduction is most likely due to the high shear rate rather than the biocide as indicated by the high level of degradation of the control. Overall BSN-1020B and BSN-1058 showed the highest degree of compatibility with almost identical performance to the control sample. The samples spike with the dilute NaOH and Tap Water also achieved results similar to the control sample, lending evidence that it may be that the high pH may be responsible for the rapid hydrolysis of the FR and thus leading to improved friction reduction. A summary of the reductions achieved is provided below in Table-2.

Example 6

Following the same general testing protocols as discussed in Example—5, combinations of SNMDC and PDMDTC were evaluated for their effect on Friction Reduction by testing with FR-516, 100 ppm added to baseline, 400 ppm added at 3 minutes, and 500 ppm added at 5 minutes.

Figure 4:
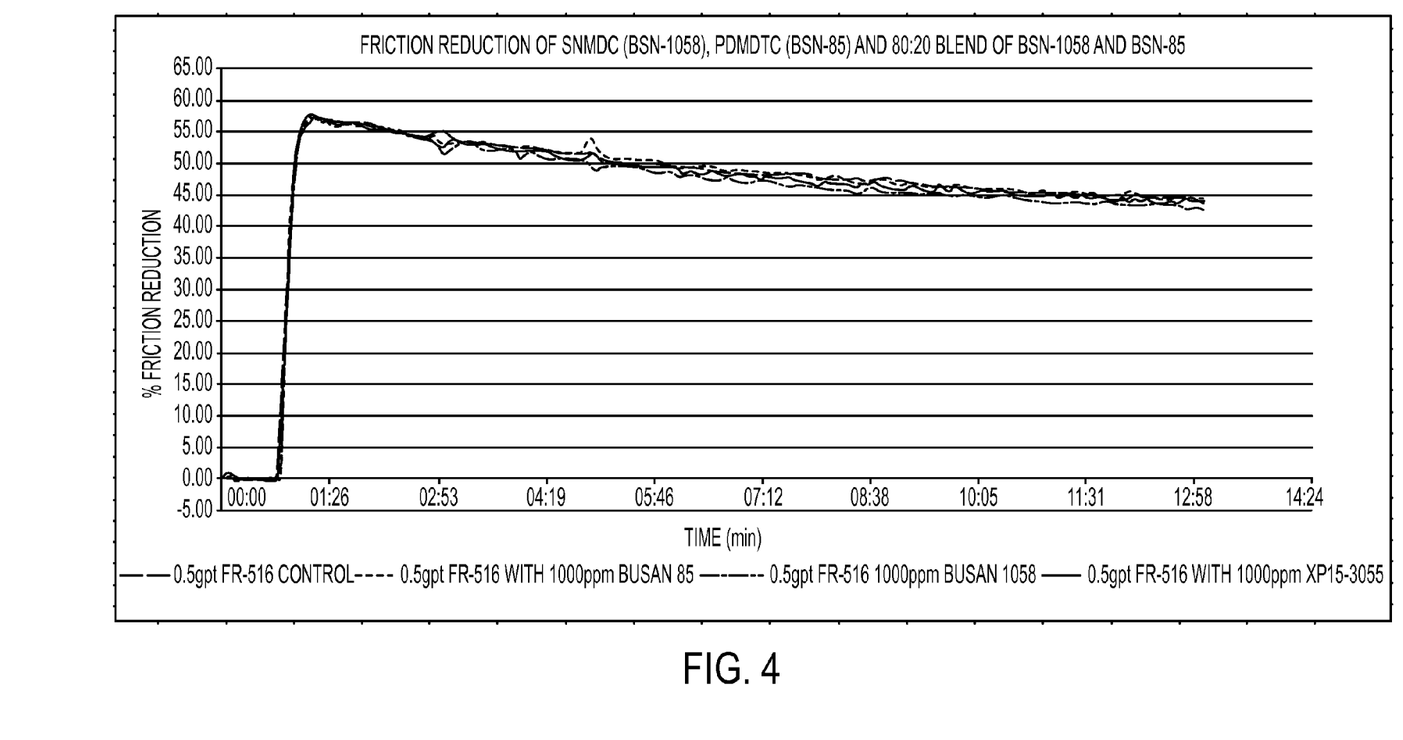
FIG. 4 is a graph illustrating results of friction reducing testing for biocide blends.

Specifically, a combination of 80% SNMDC (BSN-1058) and 20% PDMDTC (BSN-85) were blended to form the product identified as XP15-3055. The results of the Friction Reduction Testing is shown in Table-3 below. FIG. 4 shows the data graphically.

The conclusions for this blend of biocides is that there is actually an improvement in friction reduction for all of the biocides compared to the control. The higher pH of these biocides may have assisted in the hydrolysis of the friction reducing polymer.

TABLE 3

| Friction Reduction vs Time | Control | BSN-85 | XP15-3055 | BS-1058 |
|---|---|---|---|---|
| Max Redution | 56.84 | 57.1 | 57.63 | 56.95 |
| 2 minute reduction | 55.69 | 55.4 | 55.06 | 55.95 |
| 4 minute reduction | 50.68 | 52.15 | 51.81 | 52.15 |
| 6 minute reduction | 48.75 | 49.69 | 49.16 | 49.34 |
| 8 minute reduction | 46.12 | 47.48 | 46.93 | 47.31 |
| 10 minute reduction | 44.86 | 45.94 | 45.34 | 45.7 |
| 13 minute reduction | 42.75 | 44.24 | 43.92 | 44.24 |
| Total Loss in Reduction (%) | 24.78888 | 22.52189 | 23.789693 | 22.3178227 |

When an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stages, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention

TABLE 2

| Friction Reduction vs. Time | Control | BSN-85 | BSN-1020A | BSN-1020B | BSN-1058 | BSN-1020B Duplicate | Dilute NaOH | Tap Water |
|---|---|---|---|---|---|---|---|---|
| Max Reduction | 57.0 | 56.0 | 56.2 | 56.7 | 56.7 | 56.8 | 56.9 | 56.3 |
| 2 Minute Reduction | 55.5 | 54.6 | 54.6 | 54.9 | 55.0 | 55.2 | 54.7 | 55.2 |
| 4 Minute Reduction | 49.8 | 49.1 | 49.4 | 49.9 | 50.3 | 50.4 | 50.1 | 49.3 |
| 6 Minute Reduction | 46.7 | 45.7 | 46.1 | 46.3 | 46.4 | 47.1 | 46.7 | 46.1 |
| 8 Minute Reduction | 44.2 | 43.2 | 43.6 | 44.1 | 44.5 | 44.6 | 44.6 | 44.2 |
| 10 Minute Reduction | 42.1 | 41.2 | 41.8 | 42.7 | 42.5 | 43.2 | 42.3 | 42.3 |
| 13 Minute Reduction | 40.8 | 39.1 | 39.6 | 40.7 | 40.5 | 41.1 | 40.9 | 40.1 |
| Total Loss in Reduction | 28.4% | 30.2% | 29.5% | 28.2% | 28.6% | 27.6% | 28.1% | 28.8% |

The invention claimed is:

1. A composition comprising (a) an effective microbial inhibiting amount of a combination comprising (i) monomethyldithiocarbamate (MMDTC) or a salt thereof and (ii) dimethyldithiocarbamate (DMDTC) or a salt thereof, and (b) a polymer.

2. The composition of claim 1, wherein the polymer is selected from one or more of the group consisting of galactomannan polymers, derivatized galactomannan polymers, starch, xanthan gums, hydroxycelluloses, hydroxyalkyl celluloses, polyglycosans, carboxyalkyl ethers, polyvinyl alcohol polymers, copolymers of vinyl alcohol and vinyl acetate, and polymers that are a product of a polymerization reaction comprising one or more monomers selected from the group consisting of vinyl pyrrolidone, 2-acrylamido-2-methylpropanesulfonic acid, acrylic acid, and acrylamide.

3. The composition of claim 1, wherein (i) and/or (ii) is present as a solid, emulsion, or a solution.

4. The composition of claim 1, wherein (i) and/or (ii) comprises a sodium or potassium salt.

5. The composition of claim 1, (i) comprises sodium monomethyldithiocarbamate.

6. The composition of claim 1, wherein (i) comprises potassium monomethyldithiocarbamate.

7. The composition of claim 1, wherein the (i) comprises a mixture of sodium and potassium monomethyldithiocarbamate.

8. The composition of claim 1, wherein (i) comprises sodium monomethyldithiocarbamate and (ii) comprises potassium dimethyldithiocarbamate.

9. The composition of claim 8, wherein (i) and (ii) are present in amounts such that there is a synergistic effect on the inhibition of bacterial growth.

10. The composition of claim 1, wherein (i) comprises a potassium monomethyldithiocarbamate and (ii) comprises sodium dimethyldithiocarbamate.

11. The composition of claim 1, wherein the combination biocide comprises a weight ratio of sodium or potassium monomethyldithiocarbamate (MMDTC) to sodium or potassium dimethyldithiocarbamate (DMDTC) of from 10:90 to 95:5.

12. The composition of claim 1, wherein the combination comprises a weight ratio of sodium or potassium monomethyldithiocarbamate (MMDTC) to sodium or potassium dimethyldithiocarbamate (DMDTC) of from 70:30 to 30:70.

13. The composition of claim 1, wherein (i) and (ii) are present in synergistically effective amounts to inhibit bacterial growth.

14. The composition of claim 1, further comprising an additional biocide, which acts quicker than said MMDTC and/or DMDTC.

15. The composition of claim 14, wherein the additional biocide is glutaraldehyde.

16. The composition of claim 1, wherein the composition further comprises one or more additives selected from the group consisting of oils, salts, crosslinkers, additional polymers, corrosion inhibitors and dissolvers, pH modifiers, metal chelators, metal complexors, antioxidants, wetting agents, polymer stabilizers, clay stabilizers, scale inhibitors and dissolvers, wax inhibitors and dissolvers, asphaltene precipitation inhibitors, water flow inhibitors, sand consolidation chemicals, proppants, permeability modifiers, viscoelastic fluids, gases, foaming agents, and mixtures thereof.

17. A method for inhibiting bacterial contamination, comprising bringing an effective microbial inhibiting amount of (i) monomethyldithiocarbamate (MMDTC) or salt thereof and (ii) dimethyldithiocarbamate (DMDTC) or salt thereof, into contact with the bacteria to be inhibited.

18. The method according to claim 17, further comprising injecting (i) and (ii) into an injection zone, wherein the injection zone comprises a) a geologically produced material that contains one or more solid, liquid, or gaseous hydrocarbons; b) a hydrocarbon deposit; c) a petroleum deposit; d) a hydrocarbon or petroleum product formation; e) a hydrocarbon, or petroleum containing product; f) a hydrocarbon, or petroleum extraction site including drilling, hydraulic fracturing, production, stimulation, and/or disposal sites; g) hydrocarbon or petroleum transportation facility or storage equipment including pipeline, mobile tanker loading facilities, storage tanks and/or h) a refining facility, products, processes, equipment, or combinations thereof; and waters and fluids associated with: drilling, stimulation, production, hydraulic fracturing, and disposal.

19. The method according to claim 18, further comprising injecting a relatively quick-kill biocide compared to said MMDTC and/or DMDTC, into the injection zone, followed by injection of said (i) and (ii).

20. The method of claim 19, wherein the additional biocide is glutaraldehyde.

21. The method according to claim 17, comprising injecting a composition comprising (i) and (ii) into an injection zone comprising (i) makeup waters or fluids (ii) recycled waters or fluids (iii) flowback waters or fluids, (iv) injection waters or fluids, (v) produced waters or fluids or (vi) other waters or fluids; found or employed in oil field: drilling; stimulation; hydraulic fracturing; production and/or disposal operations, in an amount sufficient to reduce, inactivate, destroy, or eliminate microbes of interest.

22. The method of claim 17, wherein (i) comprises sodium monomethyldithiocarbamate and (ii) comprises potassium dimethyldithiocarbamate.

23. The method according to claim 17, wherein (i) and (ii) are present in amounts such that there is a synergistic effect on the inhibition of bacterial growth.

24. A composition comprising an effective microbial inhibiting amount of (a) monomethyldithiocarbamate (MMDTC) or a salt thereof, and (b) dimethyldithiocarbamate (DMDTC) or a salt thereof, and optionally a polymer.

25. The composition of claim 24, wherein the weight ratios of (a) to (b) is from 80:20 to 20:80, and (a) and (b) act synergistically to control bacteria.

26. The composition of claim 24, comprising a polymer.

27. The composition of claim 24, wherein the weight ratios of (a) to (b) is from 10:90 to 95:5, and (a) and (b) act synergistically to control bacteria.

* * * * *